US007371565B2

(12) United States Patent
Imaizumi et al.

(10) Patent No.: US 7,371,565 B2
(45) Date of Patent: May 13, 2008

(54) APPARATUS AND METHOD FOR MEASURING INTRACELLULAR REACTIONS

(75) Inventors: Yuji Imaizumi, Nagoya (JP); Takayuki Suga, Tokyo (JP); Yoshitaro Nakano, Shizuoka-ken (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 10/671,721

(22) Filed: Sep. 29, 2003

(65) Prior Publication Data

US 2004/0063089 A1    Apr. 1, 2004

(30) Foreign Application Priority Data

Sep. 30, 2002    (JP)    ............................. 2002-285984

(51) Int. Cl.
*C12M 1/34*    (2006.01)
(52) U.S. Cl. ................................ 435/288.7; 435/286.2; 382/133
(58) Field of Classification Search .................. 435/29, 435/808, 288.7; 250/461.2; 382/133
See application file for complete search history.

(56) References Cited

U.S. PATENT DOCUMENTS

| 5,811,251 A | * | 9/1998 | Hirose et al. ................... 435/8 |
| 6,342,379 B1 | * | 1/2002 | Tsien et al. ............... 435/173.4 |
| 2003/0100059 A1 | * | 5/2003 | Yao et al. ................... 435/69.1 |

FOREIGN PATENT DOCUMENTS

JP    09-005243    1/1997

OTHER PUBLICATIONS

Tang et al., "Development and Evaluation of High Throughput Functional Assay Methods for hERG Potassium Channel", *Journal of Biomolecular Screening*, vol. 6, No. 5, pp. 325-331 (2001).

Kain et al., "Green Fluorescent Protein as a Reporter of Gene Expression and Protein Localization", *BioTechniques*, vol. 19, No. 4, pp. 650-655 (1995).

Yamada et al., "Usefulness and Limitation of DiBAC$_4$(3), a Voltage-Sensitive Fluorescent Dye, for the Measurement of Membrane Potentials Regulated by Recombinant Large Conductance Ca$^{2+}$-Activated K$^+$ Channels in HEK293 Cells", *Jpn. J. Pharmacol.*, vol. 86, pp. 342-350 (2001).

Trouet et al., "Use of a bicistronic GFP-expression vector to characterise ion channels after transfection in mammalian cells", *Pflügers Arch—Eur J Physio*, vol. 434, pp. 632-638 (1997).

Plautz et al., "Green fluorescent protein and its derivatives as versatile markers for gene expression in living *Drosophia melanogaster*, plant and mammalian cells", *Gene*, vol. 173, pp. 83-87 (1996).

(Continued)

*Primary Examiner*—William H. Beisner
(74) *Attorney, Agent, or Firm*—Morgan, Lewis & Bockius LLP

(57) ABSTRACT

An intracellular-reaction measuring apparatus for measuring intracellular reactions by the use of a specimen in which a plurality of cell colonies are contained in a non-contact state, the apparatus includes a device that specifies the intensity of first light emitted from the specimen in accordance with the presence of a stated protein is detected to specify, of the plurality of cell colonies, a noted colony containing cells where the stated protein is present, and a device in which the intensity of second light emitted from the specimen in accordance with the intracellular reactions is detected to select, of the detected intensity of the second light, the intensity of the second light emitted from the noted colony.

11 Claims, 8 Drawing Sheets

OTHER PUBLICATIONS

Chalfie et al., "Green Fluorescent Protein as a Marker for Gene Expression", *Science*, vol. 263, pp. 802-805 (1994).

Epps et al., "Characterization of the steady-state and dynamic fluorescence properties of the potential-sensitive dye *bis*-(1,3-dibutylbarbituric acid)trimethine oxonol ($Dibac_4(3)$) in model systems and cells", *Chemistry and Physics of Lipids*, vol. 69, pp. 137-150 (1994).

Bräuner et al., "Comparative Measurements Of Membrane Potentials With Microelectrodes and Voltage-Sensitive Dyes", *Biochimica et Biophysica Acta*, vol. 771, pp. 208-216 (1984).

Gopalakrishnan et al., "Characterization of the ATP-Sensitive Potassium Channels ($K_{ATP}$) Expressed in Guinea Pig Bladder Smooth Muscle Cells", *The Journal of Pharmacology and Experimental Therapeutics*, vol. 289, No. 1, pp. 551-558 (1999).

Langheinrich et al., "Hyperpolarization of isolated capillaries from guinea-pig heart induced by $K^+$ channel openers and glucose deprivation", *Journal of Physiology*, vol. 502.2, pp. 397-408 (1997).

\* cited by examiner

APPARATUS AND METHOD FOR MEASURING INTRACELLULAR REACTIONS

This application claims the benefit of Japanese Patent application No. 2002-285984 which is hereby incorporated by reference.

BACKGROUND OF THE INVENTION

1. Field of the Invention

This invention relates to an intracellular-reaction measuring apparatus, and an intracellular-reaction measuring method, for measuring intracellular reactions by optical means. More particularly, this invention relates to an intracellular-reaction measuring apparatus and an intracellular-reaction measuring method which are suited for screening carried out in the course of developing phamaceuticals.

2. Related Background Art

Conventionally, optical measurement for intracellular reactions, e.g., changes in membrane potential as well as changes in ion concentration, has been made by en bloc detecting in a measurement visual field the intensity of light emitted from a specimen containing cells in a large number (see, e.g., Japanese Patent No. 3172060). Typical photodetectors for such en bloc detection include photomultiplier tubes and photodiodes.

For example, when the membrane potential changes are measured, a membrane-potential-sensitive fluorescent dye is previously introduced as a specimen. Also, when the ion concentration changes are measured, an ion-concentration-sensitive fluorescent dye is previously introduced as a specimen. These fluorescent dyes are fluorescent probes for measuring the intracellular reactions, and emit fluorescence having an intensity which differs depending on the membrane potential changes or ion concentration changes. Hence, the membrane potential changes or ion concentration changes can be detected by detecting the intensity of fluorescence emitted from the specimen.

However, in the above conventional method, the intensity of light (e.g., fluorescence) emitted from all cells present in the measurement visual field are en bloc detected, namely, an average light intensity in the measurement visual field is detected. Hence, where cells with a high reactivity and cells with a low reactivity are mixedly present in the measurement visual field, this makes low the sensitivity and reproducibility in the measurement of intracellular reactions.

In order to improve the sensitivity and reproducibility in the measurement of intracellular reactions, one may think of so preparing a specimen that it may contain only the cells with a high reactivity. However, it requires a very complicated operation to do so, and takes vast labor and time. That is, it is not practical to prepare such a sample containing only the cells with a high reactivity.

SUMMARY OF THE INVENTION

An object of the present invention is to provide an intracellular-reaction measuring apparatus, and an intracellular-reaction measuring method, which can improve the sensitivity and reproducibility in the measurement of intracellular reactions, without making any complicated operation for preparing specimens.

According to a first aspect of the present invention which can achieve the above object, an intracellular-reaction measuring apparatus is provided which is an intracellular-reaction measuring apparatus for measuring intracellular reactions by the use of a specimen in which a plurality of cell colonies are contained in a non-contact state; the apparatus comprising:

specifying means in which the intensity of first light emitted from the specimen in accordance with the presence of a stated protein is detected to specify, of the plurality of cell colonies, a noted colony containing cells where the stated protein is present; and selection means in which the intensity of second light emitted from the specimen in accordance with the intracellular reactions is detected to select, of the detected intensity of the second light, the intensity of the second light emitted from the noted colony.

According to a second aspect of the present invention, an intracellular-reaction measuring apparatus is provided which is an intracellular-reaction measuring apparatus for measuring intracellular reactions by the use of a specimen in which a plurality of cells are contained; the apparatus comprising:

specifying means in which the intensity of first light emitted from the specimen in accordance with the presence of a stated protein is detected to specify, of the plurality of cells, a noted cell where the stated protein is present; and selection means in which the intensity of second light emitted from the specimen in accordance with intracellular reactions induced by the protein is detected to select, of the detected intensity of the second light, the intensity of the second light emitted from the noted cell.

According to a third aspect of the present invention, an intracellular-reaction measuring apparatus is provided which is an intracellular-reaction measuring apparatus for measuring intracellular reactions by the use of a specimen in which a plurality of cells stand adherent to one another; the apparatus comprising:

specifying means in which the intensity of first light emitted from the specimen in accordance with the presence of a stated protein is detected to specify a noted region having cells where the stated protein is present, in a higher proportion than a stated standard proportion; and selection means in which the intensity of second light emitted from the specimen in accordance with intracellular reactions induced by the protein is detected to selection, of the detected intensity of the second light, the intensity of the second light emitted from the noted region.

According to a fourth aspect of the present invention, an intracellular-reaction measuring method is provided which is an intracellular-reaction measuring method for measuring intracellular reactions caused by chemical substances, by the use of a specimen in which a plurality of cell colonies are contained in a non-contact state; the method comprising:

a preparation step in which a specimen is prepared by incorporating into a cell a gene of a protein serving as a target of the chemical substances and a gene of a fluorescent protein, culturing the cell, and thereafter incorporating a fluorescent probe for measuring intracellular reactions;

a specifying step in which the intensity of first fluorescence emitted from the fluorescent protein having been expressed together with the target protein is detected to specify, of the plurality of cell colonies, a noted colony containing cells where the target protein is present; and a selection step in which the intensity of second fluorescence emitted from the fluorescent probe is detected to select, of the detected intensity of the second fluorescence, the intensity of the second fluorescence emitted from the noted colony.

According to a fifth aspect of the present invention, an intracellular-reaction measuring method is provided which is an intracellular-reaction measuring method for measuring intracellular reactions caused by chemical substances, by the use of a specimen in which a plurality of cells stand adherent to one another; the method comprising:

a preparation step in which a specimen is prepared by incorporating into a cell a gene of a protein serving as a target of the chemical substances and a gene of a fluorescent protein, culturing the cell, and thereafter incorporating a fluorescent probe for measuring intracellular reactions;

a specifying step in which the intensity of first fluorescence emitted from the fluorescent protein having been expressed together with the target protein is detected to specify a target region having cells where the target protein is present, in a higher proportion than a stated standard proportion; and a selection step in which the intensity of second fluorescence emitted from the fluorescent probe is detected to select, of the detected intensity of the second fluorescence, the intensity of the second fluorescence emitted from the noted region.

According to a sixth aspect of the present invention, an intracellular-reaction measuring method is provided which is an intracellular-reaction measuring method for measuring intracellular reactions caused by chemical substances, by the use of a specimen in which a plurality of cells are contained; the method comprising:

a preparation step in which a specimen is prepared by incorporating into a cell a gene of a protein serving as a target of the chemical substances and a gene of a fluorescent protein, culturing the cell, and thereafter incorporating a fluorescent probe for measuring intracellular reactions;

a specifying step in which the intensity of first fluorescence emitted from the fluorescent protein having been expressed together with the target protein is detected to specify, of the plurality of cells, a noted cell where the target protein is present; and a selection step in which the intensity of second fluorescence emitted from the fluorescent probe is detected to select, of the detected intensity of the second fluorescence, the intensity of the second fluorescence emitted from the noted cell.

BRIEF DESCRIPTION OF THE DRAWINGS

FIGS. 3A and 3B are diagrammatic views to illustrate two cell colonies 23(1) and 23(2) included in a measurement visual field 10a.

DESCRIPTION OF THE PREFERRED EMBODIMENTS

Embodiments of the present invention are described below in detail with reference to the accompanying drawings.

First Embodiment

As First Embodiment of the present invention, an example of an intracellular-reaction measuring apparatus is described with which any membrane potential changes caused by chemical substances can be measured in a high sensitivity and a good reproducibility.

In this connection, the "membrane" of the membrane potential changes refers to a membrane present within a cell (e.g., a cell membrane, a mitochondrion membrane or a nuclear membrane). The "membrane potential" refers to the potential inside the membrane with respect to that outside the membrane. Herein, the membrane potential referred to in this First Embodiment and Second, Third and Fifth Embodiments given later is the cell membrane potential.

Figure 1:
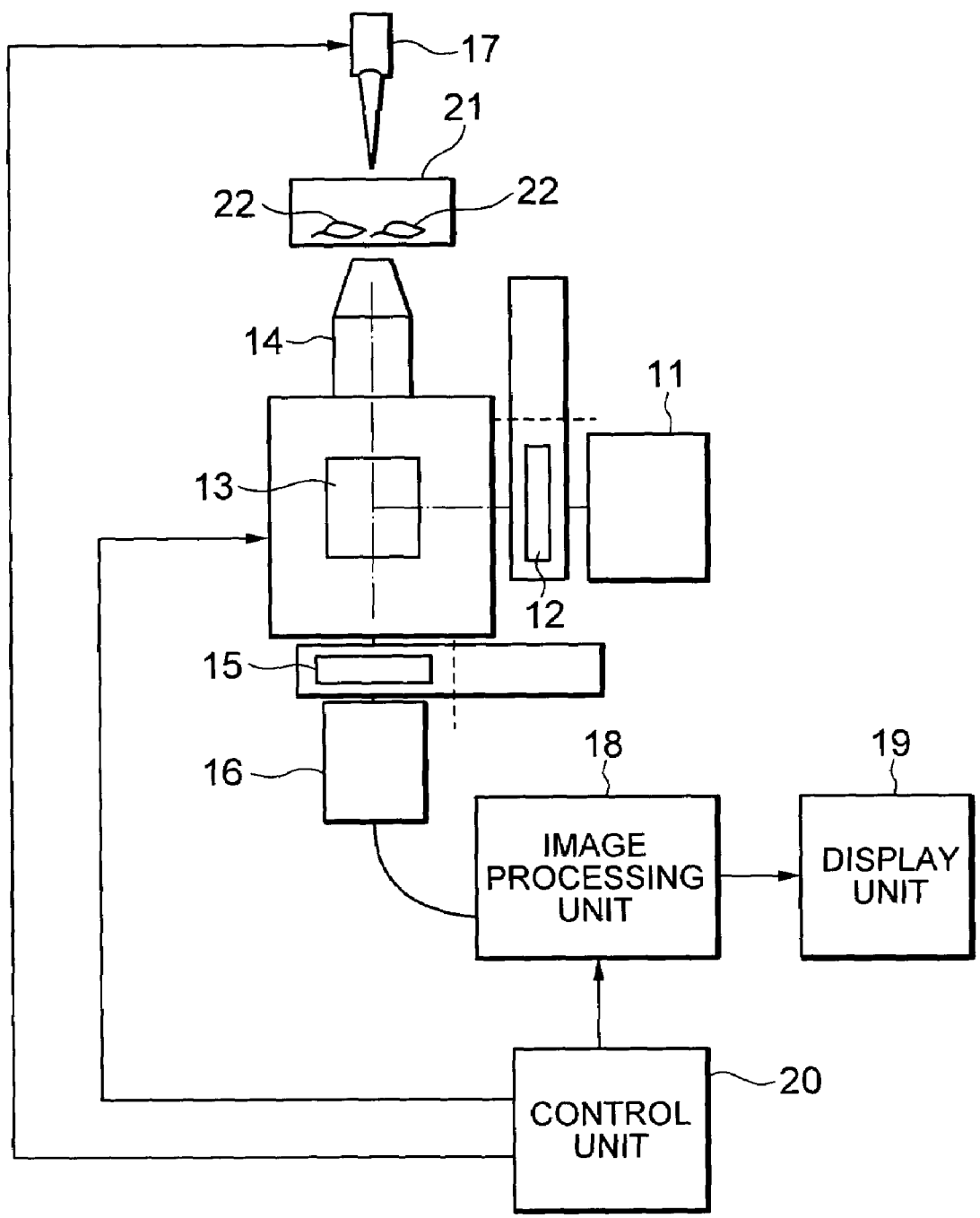
FIG. 1 is a schematic view showing the whole configuration of an intracellular-reaction measuring apparatus 10 of the present invention.

An intracellular-reaction measuring apparatus 10 of First Embodiment is, as shown in FIG. 1, constituted of an inverted-type fluorescent microscope (11-16), a pipette 17 for introducing chemical substances, an image processing unit 18, a display unit 19 and a control unit 20. In a memory provided in the control unit 20, an intracellular-reaction measuring program is kept installed in which the procedure of measuring membrane potential changes caused by chemical substances has been depicted.

The fluorescent microscope (11-16) is provided with a light source 11, an excitation filter 12, a dichroic mirror 13, an objective lens 14, a fluorescence filter 15 and a cooled CCD camera 16. At the upper part of the objective lens 14, a stage (not shown) is provided which supports a laboratory dish 21. The laboratory dish 21 is a culture vessel the bottom of which is transparent and in which a specimen containing a plurality of culture cells 22 are held.

Before the respective constituents 11 to 20 of the intracellular-reaction measuring apparatus 10 of First Embodiment are described, the specimen (a plurality of culture cells 22) held in the laboratory dish 21 is described first. The specimen is prepared according to the following procedure consisting of steps (1) to (3).

Step (1):

In the first place, an expression vector containing a gene of a protein serving as a target (hereinafter "target protein")

of chemical substances and a gene of a fluorescent protein is made up. Using this expression vector, genes are incorporated into culture cells. The target protein refers to an ion channel or a receptor, and is a protein which induces membrane potential changes. The fluorescent protein refers to a protein having fluorescent properties.

In a specific measurement example given later, a small-conductance $Ca^{2+}$-dependent $K^+$ channel (hereinafter "rSK2 channel") derived from a rat is used as the target protein, and, as known chemical substances which act on the target protein, 300 μM chlorzoxazone (an rSK2 channel opener) and 100 nM apamin (an rSK2 channel inhibitor) are used. Green Fluorescence Protein (hereinafter "GFP") is used as the fluorescent protein.

The ion channel such as the rSK2 channel is a factor indispensable for forming membrane potential of all sorts of cells of living bodies. In particular, in cells such as nerves, sinews and secretors, it acts as a very important factor in order to exhibit cytophysiological functions such as generation, transport and transfer of living-body electric signals, and contraction, as well as secretion of physiological substances such as hormones.

Ion channel agonists such as ion channel openers or inhibitors have already been put into use for the purpose of recovering and controlling any tissue functional disorders, in treating many serious diseases such as arrhythmia, hypertension and diabetes. In more recent years, using ion channels as targets, it is attempted to develop new medicines aiming at protection of the central nerves from ischemic disorder or at treatment of various diseases such as tonic bladder, respiratory tract hypersensitiveness, enterokinesis failure, and atopic dermatitis.

Step (2):

Next, the above culture cells into which the expression vector has been incorporated and the gene of target protein and the gene of fluorescent protein have been incorporated are cultured in the laboratory dish 21. Usually, the culture cells continue to multiply, forming cell colonies. Accordingly, culture conditions and culture time may be controlled so that they can be cultured in such a way that the cell colonies do not adhere to one another.

Figure 2:
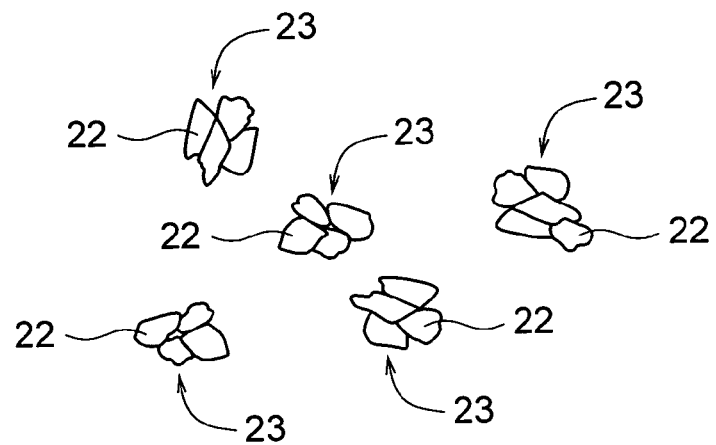
FIG. 2 is a diagrammatic view to illustrate a plurality of cell colonies 23 contained in a specimen.

As the result, as shown in FIG. 2, it follows that in the specimen held in the laboratory dish 21 a plurality of cell colonies 23 are contained in a non-contact state. Culture cells 22 in each cell colony 23 are in a number of several to tens. The culture cells 22 themselves of each cell colony 23 stand adherent to one another. Incidentally, the space between mutual cell colonies 23 is filled with a culture solution.

Thus, the specimen is so cultured that a plurality of cell colonies 23 are contained in a non-contact state. This is done in order that the membrane potential changes caused by chemical substances are measured for each cell colony 23 in the intracellular-reaction measuring apparatus 10 of First Embodiment.

In the specimen (see FIG. 2), in some culture cells 22, the target protein (e.g., rSK2 channel) comes expressed on the surfaces of membranes. The fluorescent protein (e.g., GFP) further comes expressed on substantially all the culture cells 22 on which the target protein has come expressed. Hence, the target protein and the fluorescent protein always come expressed together in one culture cell 22.

Hence, the presence of the target protein can be verified on the basis of the presence or absence of the fluorescence emitted from the fluorescent protein. That is, it can be considered that the target protein stands expressed in the culture cell 22 where the fluorescence from the fluorescent protein has appeared (detailed later).

In a culture cell 22 in which the target protein has come expressed (hereinafter "expressed cell"), upon introduction of a chemical substance (e.g., an agonist such as the rSK2 channel opener) at the time of the measurement described later, the chemical substance causes changes in membrane potential. On the contrary, in a culture cell 22 in which the target protein has not come expressed, basically the chemical substance causes no changes in membrane potential even when it is introduced.

It, however, has been found that the membrane potential changes caused by chemical substances take place not only in the expressed cell but also as a whole in each cell colony 23 containing the expressed cell. In the cell colony 23, the changes in membrane potential in the expressed cell spread to adjoining non-expressed cells in virtue of the contact of culture cells 22 with one another, as so considered.

In the intracellular-reaction measuring apparatus 10 of First Embodiment, this nature is utilized, and the membrane potential changes caused by chemical substances are measured for each cell colony 23. Hence, even when expressed cells are in a small proportion (a low expression efficiency) and fluctuate greatly, the membrane potential changes caused by chemical substances can be measured in a high sensitivity and a good reproducibility (detailed later). This makes it unnecessary to make any complicated and time-consuming operation for preparing a specimen, such as the preparation of a cell specimen in which the target protein is steadily expressed.

Step (3):

As a final step for the operation of preparing the specimen, a fluorescent probe to be used to measure intracellular reactions is introduced all over into the specimen (the plurality of cell colonies 23) held in the laboratory dish 21. In this Embodiment, this fluorescent probe is a membrane-potential-sensitive fluorescent dye. This fluorescent dye includes those for measuring the absolute value of membrane potential and those for measuring relative changes of membrane potential.

In a specific measurement example given later, an oxonol type dye bis-(1,2-dibutylbarbituric acid)-trimethine oxonol (hereinafter "$DiBAC_4(5)$") is used as the fluorescent dye. The fluorescence emitted from this $DiBAC_4(5)$ has a wave range different from that of the fluorescence emitted from the above GFP. Hence, these two types of fluorescence can be detected with clear distinction from each other.

Thus, since the membrane-potential-sensitive fluorescent dye [e.g., $DiBAC_4(5)$] is introduced into the whole specimen, the fluorescence is emitted from the fluorescent probe having been introduced, without regard to which is the cell where the target protein has been expressed or the cell where it has not, in all the culture cells 22 contained in the specimen. Hence, the presence of all the culture cells 22 (i.e., the plurality of cell colonies 23) can be verified on the basis of the presence or absence of the fluorescence emitted from the membrane-potential-sensitive fluorescent probe.

Upon introduction of a chemical substance at the time of the measurement described later, the membrane-potential-sensitive fluorescent dye [e.g., $DiBAC_4(5)$] emits fluorescence having intensity which differs depending on the membrane potential changes caused by chemical substances. As described already, the changes in membrane potential take place as a whole in the cell colonies 23 containing expressed cells, and hence, changes in intensity of the fluorescence emitted from the membrane-potential-sensitive fluorescent dye also take place as a whole in the cell colonies 23 containing expressed cells.

On the other hand, in a cell colony 23 containing no expressed cell, the changes in membrane potential do not take place even when chemical substances are introduced, and hence basically the intensity of the fluorescence emitted from the membrane-potential-sensitive fluorescent dye also does not change. However, a little change in intensity may occur as an artifact (noise component).

As described above, in the specimen prepared through the above steps (1) to (3), the plurality of cell colonies 23 are contained in a non-contact state (see FIG. 2), and also the expressed cells having the target protein (e.g., rSK2 channel) and the fluorescent protein (e.g., GFP) together are contained in a usual expression efficiency (e.g., approximately 20% to 30%), and still also the membrane-potential-sensitive fluorescent probe [e.g., $DiBAC_4(5)$] is over all introduced into the specimen.

The intracellular-reaction measuring apparatus 10 is described below. In the intracellular-reaction measuring apparatus of First Embodiment, the fluorescence emitted from the fluorescent protein (e.g., GFP) contained in the specimen and the fluorescence emitted from the membrane-potential-sensitive fluorescent dye [e.g., $DiBAC_4(5)$] are detected with distinction from each other. Accordingly, the excitation filter 12, the dichroic mirror 13 and the fluorescence filter 15 (generically called "filter set") of the fluorescent microscope (11-16) are set switchable.

A filter set that is best suited for detecting the fluorescence emitted from, e.g., the GFP is a combination of an excitation filter 12 capable of transmitting light with wavelengths ranging from 470 nm to 490 nm, a dichroic mirror 13 capable of reflecting light with wavelengths shorter than 505 nm and transmitting light with wavelengths of 505 nm and longer, and a fluorescence filter 15 capable of transmitting light with wavelengths ranging from 520 nm to 560 nm.

A filter set that is best suited for detecting the fluorescence emitted from the $DiBAC_4(5)$ is a combination of an excitation filter 12 capable of transmitting light with wavelengths ranging from 540 nm to 580 nm, a dichroic mirror 13 capable of reflecting light with wavelengths shorter than 595 nm and transmitting light with wavelengths of 595 and longer, and a fluorescence filter 15 capable of transmitting light with wavelengths ranging from 600 nm to 660 nm.

In the intracellular-reaction measuring apparatus 10 of First Embodiment, the switching between the filter set for fluorescent protein (e.g., GFP) and the filter set for membrane-potential-sensitive fluorescent dye [e.g., $DiBAC_4(5)$] is automatically operated in accordance with control signals sent from the control unit 20.

In the intracellular-reaction measuring apparatus 10, when the filter set for GFP is kept inserted to the fluorescent microscope (11-16), the specimen (the plurality of cell colonies 23) held in the laboratory dish 21 is episcopic-illuminated through this filter set and the objective lens 14, and the GFP in the expressed cells is excited. Excitation light has a center wavelength of 480 nm. Incidentally, the objective lens 14 is, e.g., an oil immersion objective lens of 40 maginifications.

The fluorescence (center wavelength: about 510 nm; green) emitted from the GFP in the expressed cells also enters the cooled CCD camera 16 through the objective lens 14 and the filter set (for GFP). In the cooled CCD camera 16, it photographs a specimen image (an image of expressed cells) on the basis of the fluorescence emitted from the GFP, and outputs a fluorescent image to the image processing unit 18.

Meanwhile, when the filter set for $DiBAC_4(5)$ is kept inserted to the fluorescent microscope (11-16), the specimen held in the laboratory dish 21 is episcopic-illuminated through this filter set and the objective lens 14, and the $DiBAC_4(5)$ in all the expressed cells is excited. Excitation light has a center wavelength of 560 nm.

The fluorescence (center wavelength: 630 nm; red) emitted from the $DiBAC_4(5)$ in all the expressed cells enters the cooled CCD camera 16 through the objective lens 14 and the filter set [for $DiBAC_4(5)$]. In the cooled CCD camera 16, it photographs a specimen image (an image of cell colonies 23) on the basis of the fluorescence emitted from the $DiBAC_4(5)$, and outputs a fluorescent image data to the image processing unit 18.

Thus, in the intracellular-reaction measuring apparatus 10, the combination of the filter set may only be switched in accordance with the control signals sent form the control unit 20, whereby the fluorescent image of expressed cells that is based on the fluorescent protein (e.g., GFP) and the fluorescent image of cell colonies 23 that is based on the membrane-potential-sensitive fluorescent dye [e.g., $DiBAC_4(5)$] can be captured one by one.

In the intracellular-reaction measuring apparatus 10, the fluorescent image of expressed cells that is based on the fluorescent protein (e.g., GFP) is captured only once, and the fluorescent image of cell colonies 23 that is based on the membrane-potential-sensitive fluorescent dye [e.g., $DiBAC_4(5)$] is repeatedly captured at intervals of a constant time (e.g., at intervals of 10 seconds). Such two types of operation of image capture are automatically switched in accordance with the control signals sent form the control unit 20.

Each fluorescent image is recorded in a memory (e.g., a hard disk) provided in the image processing unit 18, and is read as occasion calls at the time of the subsequent image processing (i.e., in forming measurement information relating to the changes in membrane potential as described later). Each fluorescent image is also appropriately displayed on the display unit 9. The fluorescent image is in a size (corresponding to the measurement visual field) of, e.g., 210 μm×170 μm on the specimen.

In the intracellular-reaction measuring apparatus 10, in order to measure the membrane potential changes caused by chemical substances, the chemical substances (the rSK2 channel opener and inhibitor) are halfway further introduced in order, from the pipette 17 into the specimen in the laboratory dish 21 while the fluorescent images of cell colonies 23 that are based on the membrane-potential-sensitive fluorescent dye [e.g., $DiBAC_4(5)$] are repeatedly captured. The timing at which such chemical substances are introduced is automatically set in accordance with the control signals sent form the control unit 20.

In the intracellular-reaction measuring apparatus 10 of First Embodiment, the fluorescent microscope (11-16) having the filter set for fluorescent protein (e.g., GFP) and the image processing unit 18 correspond to the "specifying means" referred to in claims. Also, the fluorescent microscope (11-16) having the filter set for membrane-potential-sensitive fluorescent dye [e.g., $DiBAC_4(5)$] and the image processing unit 18 correspond to the "selection means" and "forming means" referred to in claims.

The procedure of how to measure the changes in membrane potential in the intracellular-reaction measuring apparatus 10 constructed as described above is described below with reference to FIGS. 3A, 3B and 4. As shown in FIG. 4, the procedure consists of steps S1 to S9. The control unit 20 performs measurement of the membrane potential changes caused by chemical substances, making reference to the intracellular-reaction measuring program kept installed in its interior.

Figure 3A:
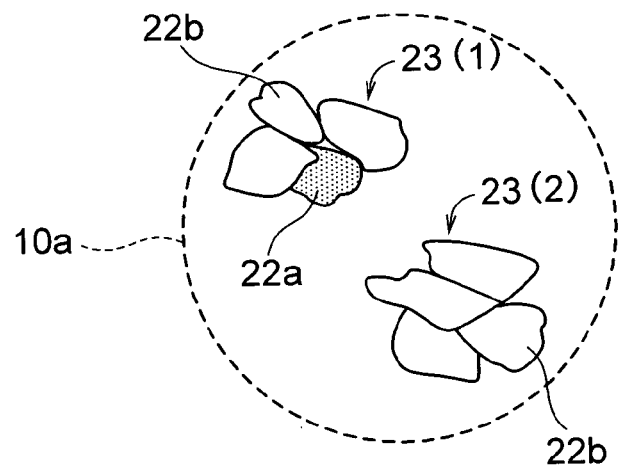
Figure 4:
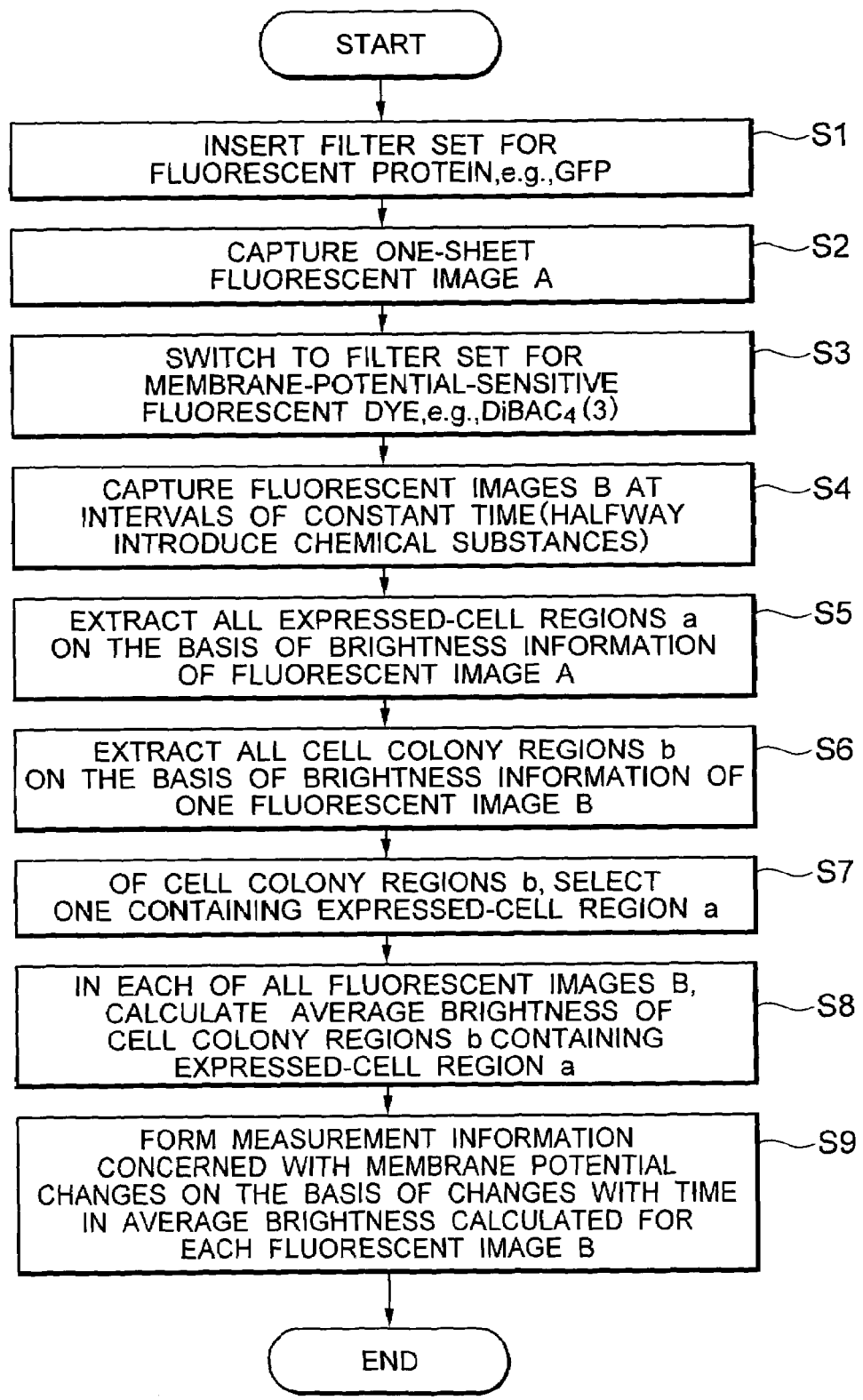
FIG. 4 is a flow chart showing the procedure of measuring changes in membrane potential in the intracellular-reaction measuring apparatus 10 of the present invention.

Here, the procedure is described assuming that as shown in FIG. 3A two cell colonies 23 are included in a measurement visual field 10a. Needless to say, the measurement can be made also when the number of the cell colony/ies 23 included in the measurement visual field 10a is one or three or more.

Assume that one cell colony 23(1) of two cell colonies 23(1) and 23(2) contains one expressed cell 22a having the target protein (e.g., rSK2 channel) and the fluorescent protein (e.g., GFP) together, and the other cell colony 23(2) contains no expressed cell 22a at all. In FIG. 3A, the expressed cell 22a is shaded. Non-expressed cells 22b are not shaded.

In the first place, the control unit 20 inserts the filter set for fluorescent protein (e.g., GFP) (step S1 in FIG. 4). Here, in the measurement visual field 10a shown in FIG. 3A, fluorescence is emitted from only the fluorescent protein of the expressed cell 22a (the shaded portion) of the cell colony 23(1).

In this state, the control unit 20 controls the cooled CCD camera 16 through the image processing unit 18, and captures one fluorescent image A (step S2) on the basis of the fluorescence emitted from the fluorescent protein of the expressed cell 22a of the cell colony 23(1), and stores it in the memory of the image processing unit 18. This fluorescent image A is used to specify the cell colony 23(1) containing the expressed cell 22a, in the measurement visual field 10a.

Figure 3B:
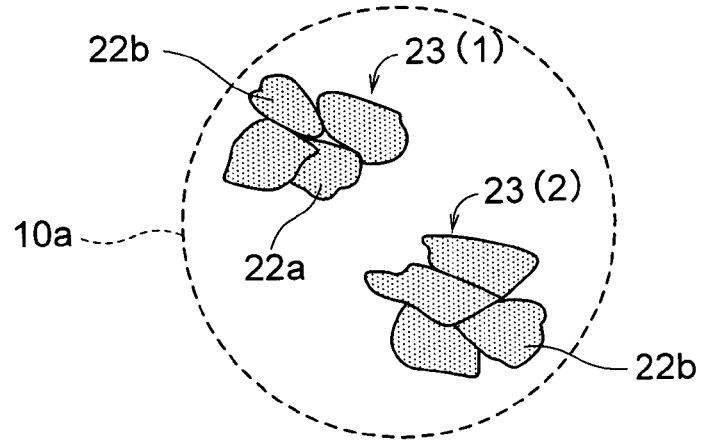

Next, the control unit 20 switches the filter unit to that for the membrane-potential-sensitive fluorescent dye [e.g., DiBAC$_4$(5)] (step S3). Here, in the measurement visual field 10a, as shown in FIG. 3B, fluorescence is emitted from the membrane-potential-sensitive fluorescent dye incorporated into all the culture cells (expressed cell 22a and non-expressed cells 22b) constituting the two cell colonies 23(1) and 23(2).

In this state, the control unit 20 controls the cooled CCD camera 16 through the image processing unit 18, and captures fluorescent images B at intervals of a constant time (e.g., 10 seconds) (step S4) on the basis of the fluorescence emitted from the membrane-potential-sensitive fluorescent dye of both the expressed cell 22a and non-expressed cells 22b, and stores them in the memory of the image processing unit 18. These fluorescent images B are used to specify the cell colonies 23(1) and 23(2) in the measurement visual field 10a and also to form measurement information of the membrane potential changes caused by chemical substances.

The control unit 20 further introduces two kinds of chemical substances from the pipette 17 into the specimen while capturing the fluorescent images B repeatedly in the step S4, halfway and at a preset timing. For example, it introduces a target protein channel opener (e.g., chlorzoxazone) and thereafter introduces a channel inhibitor (e.g., apamin), to change the composition of chemical substances in the culture solution of the specimen.

Hence, in the cell colony 23(1) containing the expressed cell 22a, the intensity of fluorescence emitted from the membrane-potential-sensitive fluorescent dye [e.g., DiBAC$_4$ (5)] changes as a whole in accordance with the introduction of chemical substances. Stated specifically, the fluorescence intensity decreases greatly upon introduction of the target protein channel opener and the intensity having decreased recovers upon introduction of the target protein channel inhibitor. Any remarkable change in intensity does not take place in the cell colony 23(2) containing no expressed cell 22a.

The control unit 20 completes capturing one fluorescent image A and a large number of fluorescent images B as the result of the above steps S1 to S4, whereupon it controls the image processing unit 18 to execute the subsequent steps S5 to S9, to form measurement information of the membrane potential changes caused by chemical substances. The fluorescent image A is an image of the expressed cell 22a. The fluorescent images B are images of the cell colonies 23(1) and 23(2).

First, in the step S5, the image processing unit 18 detects brightness information of the one fluorescent image A to thereby extract all high-brightness regions corresponding to expressed cells 22a (hereinafter "expressed-cell region(s) a") in the measurement visual field 10a. The expressed-cell region(s) a is/are extracted by binarizing the fluorescent image A. The brightness information of the fluorescent image A represents the intensity of the fluorescence emitted from the fluorescent protein (e.g., GFP).

Further, in the step S5, in all the expressed-cell regions a, the image processing unit 18 judges an area having continuously high brightness (i.e., a closed area), to be a "region corresponding to one expressed cell". In the case when only one expressed cell 22a is present as shown in FIG. 3A, the expressed-cell region a consists of one region. If two expressed cells 22a are present, it follows that two expressed-cell regions a are separately present.

In the next step S6, the image processing unit 18 selects an arbitrary one image (an image before introduction of chemical substances) from among the large number of fluorescent images B, and detects its brightness information to thereby extract all high-brightness regions corresponding to the cell colonies 23(1) and 23(2) (hereinafter "cell colony region(s) b") in the measurement visual field 10a. The cell colony region(s) b is/are also extracted by binarizing the fluorescent image B. The brightness information of the fluorescent image B selected represents the intensity of the fluorescence emitted from the membrane-potential-sensitive fluorescent dye [e.g., DiBAC$_4$ (5)].

In the step S6, in all the cell colony regions b, the image processing unit 18 judges an area having continuously high brightness (i.e., a closed area), to be a "region corresponding to one cell colony". In the case when two cell colonies 23(1) and 23(2) are present as shown in FIG. 3B, it follows that two cell colony regions b are separately present.

In the following description, in each of the fluorescent image B having been processed in the step S6 and other fluorescent images B, the area corresponding to the cell colony 23(1) in the cell colony regions b is called "cell colony region b(1), and the area corresponding to the cell colony 23(2) in the same, "cell colony region b(2)".

In the next step S7, using the results of extraction in the steps S5 and S6, the image processing unit 18 superimposes the fluorescent image A having the expressed-cell region(s) a and the fluorescent image B having the cell colony regions b(1) and b(2), and, of the cell colony regions b(1) and b(2), selects a region including at least one expressed-cell region a. For example, in the case of those shown in FIGS. 3A and 3B, only a cell colony region b(1) corresponding to the cell colony 23(1) is selected.

Then, in the next steps S8 and S9, noting the cell colony region b(1) selected, the image processing unit 18 forms the measurement information of the membrane potential changes caused by chemical substances. Here, the processing in the above steps S5 to S7 corresponds to the processing to specify a noted colony containing at least one expressed cell 22a, namely, the cell colony 23(1), of the cell colonies 23(1) and 23(2) included in the measurement visual field 10a. What is meant by "containing at least one expressed cell 22a" is "containing at least one target protein (e.g., rSK2 channel).

In the next step S8, the image processing unit 18 selectively detects the brightness information of the cell colony region b(1) selected in the step S7 from among the respective fluorescent images B captured at intervals of a constant time in the step S4, and calculates average brightness for each fluorescent image B.

Incidentally, the brightness information of the cell colony region b(1) represents the intensity of fluorescence emitted from the noted colony containing the expressed cell 22a, namely, the cell colony 23(1). The average brightness represents average intensity of the fluorescence emitted from the noted colony (in the following description, often simply "fluorescence intensity").

Then, in the final step S9, the image processing unit 18 analyzes changes with time in the average brightness calculated for each fluorescent image B (i.e., the intensity of fluorescence emitted from the noted colony containing the expressed cell 22a) to form measurement information concerned with the changes in membrane potential of the noted colony. The measurement information concerned with the changes in membrane potential of the noted colony refers to the percentage in which, e.g., the fluorescence intensity has decreased while the target protein channel opener (e.g., chlorzoxazone) is introduced and thereafter the channel inhibitor (e.g., apamin) is introduced (i.e., response rate).

Thus, in the intracellular-reaction measuring apparatus 10 of First Embodiment, the intensity of fluorescence emitted from the noted colony containing the expressed cell 22a, namely, the cell colony 23(1), of the cell colonies 23(1) and 23(2) in the measurement visual field 10a, is selectively detected, and the measurement information of the membrane potential changes caused by chemical substances is formed (e.g., response rate (per cent decrease) of fluorescence intensity is found). Hence, the changes in membrane potential can be measured in a high sensitivity and a good reproducibility.

Finally, a preparation example of a specific specimen and a measurement example making use of the specimen are described below.

The specimen is prepared according to the procedure consisting of steps (1) to (3) described previously.

In the step (1), in the first place, a gene (cDNA) of an rSK2 channel having been cloned in full length is inserted to a mammal cell expression vector Ptracer-CMV2 (Invitrogen, USA) to produce an expression vector. The Ptracer-CMV2 has originally been integrated with a gene of GFP.

Next, into a solution in which culture cells derived from a human embryonic kidny (hereinafter "HEK293 cells") (Human Science Laboratory Source Bank, Japan) are contained in a concentration of $10^5$ cells/ml, the above expression vector is introduced by calcium phosphate coprecipitation.

In the step (2), the HEK293 cells into which the gene of rSK2 channel and the gene of GFP have been incorporated by incorporating the expression vector are cultured in the laboratory dish 21. A culture medium used here is Minimum Essential Medium (Gibco BRL, USA) to which 10% fetal bovine serum (FCS; JRS Biosciences, USA) has been added. Culture time is 36 to 48 hours, and culture temperature is 37° C.

After the expression vector has been incorporated, 36 to 48 hours are allowed to elapse, and the resulting HEK293 cells are used for measurement. Here, in the laboratory dish 21, cell colonies 23 (see FIG. 2) consisting of a plurality of HEK293 cells are contained in a non-contact state. In addition, in some HEK293 cells, the rSK2 channel and the GFP stand expressed simultaneously. This expression is in an expression efficiency of, e.g., approximately from 20% to 30%.

In the step (3), the membrane-potential-sensitive fluorescent dye $DiBAC_4(5)$ (Molecular Probes, USA) is introduced all over into the specimen held in the laboratory dish 21. That is, in a physiological saline solution containing the $DiBAC_4(5)$ in a concentration of 50 nM, the HEK293 cells are immersed for about 30 minutes so as to be loaded. Such loading is continued also during the measurement of changes in membrane potential.

The measurement using the specimen having been prepared is made according to the procedure of the flow chart shown in FIG. 4 (steps S1 to S9). The measurement temperature is room temperature (24±1° C.).

To describe the following measurement example, reference is suitably made to a phase-contrast photomicrograph (FIG. 5) of the specimen. As can be seen from this photograph and FIG. 6 referred to later, two cell colonies GFP(+) and GFP(−) are included in the measurement visual field. Also, one cell colony GFP(+) contains twenty to thirty HEK293 cells, and the other cell colony GFP(−) contains four HEK293 cells.

The control unit 20 of the intracellular-reaction measuring apparatus 10 executes the steps S1 and S2 shown in FIG. 4, to capture one fluorescent image A (FIG. 6) on the basis of the fluorescence emitted from the GFP present in the measurement visual field. The fluorescent image A is an image of expressed cells (the HEK293 cells in which the rSK2 channel and the GFP stand expressed simultaneously).

Next, the control unit 20 executes the steps S3 and S4 to capture fluorescent images B (FIG. 7) at intervals of 10 seconds on the basis of the fluorescence emitted from the $DiBAC_4(5)$ present in the measurement visual field. The fluorescent images B are each an image of the cell colonies GFP(+) and GFP(−) (see also FIG. 5). Image capture of the fluorescent images B is intermittently performed for about 16 minutes.

Further, capturing the fluorescent images B repeatedly in the step S4, the control unit 20 introduces 300 μM chlorzoxazone (rSK2 channel opener) halfway and at a preset timing t1, and, at a timing t2 thereafter, introduces 100 nM apamin (rSK2 channel inhibitor).

Thus, the control unit 20 completes capturing one fluorescent image A (FIG. 6) and a large number of fluorescent images B (FIG. 7) as the result of the above steps S1 to S4, whereupon the image processing unit 18 subsequently executes the steps S5 to S9 to form the measurement information of the membrane potential changes caused by chemical substances.

More specifically, on the basis of the brightness information of the fluorescent image A (FIG. 6), the image processing unit 18 extracts all high-brightness regions (i.e., the expressed-cell region(s) a) having appeared in the fluorescent image A, for each expressed cell (step S5). In the case shown in FIG. 6, three expressed-cell regions a are present in the fluorescent image A.

Further, on the basis of the brightness information of the fluorescent image B (FIG. 7) before the introduction of chemical substances, the image processing unit 18 extracts all high-brightness regions (i.e., the cell colony region(s) b)

having appeared in the fluorescent image B, for each cell colony (step S6). In the case shown in FIG. 7, two cell colony regions b are present in the fluorescent image B. Here, as can be seen from comparison of the fluorescent image B with the FIG. 5 photograph, the two cell colony regions b correspond to the two cell colonies GFP(+) and GFP(−).

Then, subsequently, it superimposes the fluorescent image A (FIG. 6) having three expressed-cell regions a and the fluorescent image B (FIG. 7) having two cell colony regions b, and, of the two cell colony regions b, selects a region including at least one expressed-cell region (step S7).

Figure 5:
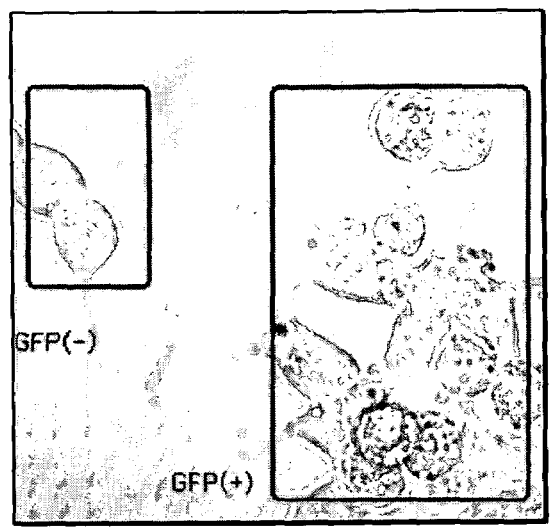
FIG. 5 is a phase-contrast photomicrograph of a specimen.
Figure 6:
FIG. 6 is a photograph of a fluorescent image captured on the basis of fluorescence emitted from GFP.
Figure 7:
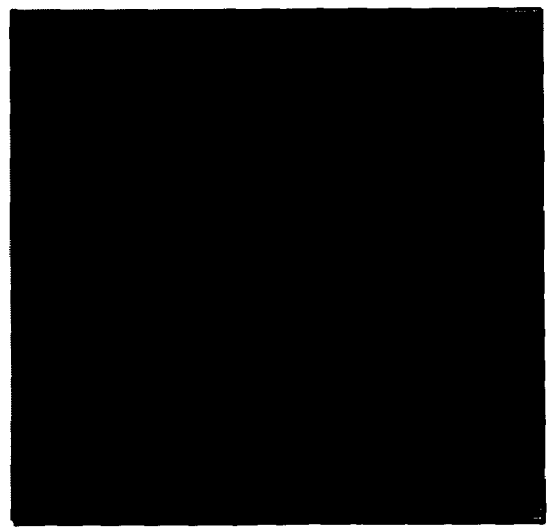
FIG. 7 is a photograph of a fluorescent image captured on the basis of fluorescence emitted from $DiBAC_4(5)$.

For example, in the case of those shown in FIGS. 5 to 7, the cell colony region b corresponding to one cell colony GFP(+) includes the three expressed-cell regions a, and hence only this cell colony region b is selected in the step S7.

Incidentally, the number of the respective expressed cells contained in the cell colonies GFP(+) and GFP(−) present in the measurement visual field can be known by the number of the expressed-cell regions a included in the cell colony region b. For example, in the case of those shown in FIGS. 5 to 7, the cell colony GFP(+) contains three expressed cells, and the cell colony GFP(−) contains no expressed cell at all.

Then, noting the cell colony region b corresponding to the cell colony GFP(+), the image processing unit 18 executes the step S8. That is, the image processing unit 18 selectively detects the brightness information of the cell colony region b corresponding to the cell colony GFP(+), from among the large-number fluorescent images B (FIG. 7), and calculates the average brightness for each fluorescent image B. That is, it calculates the intensity of fluorescence emitted from the cell colony GFP(+).

Finally, it finds changes with time (FIG. 8) in the average brightness calculated for each fluorescent image B, i.e., in the intensity of fluorescence emitted from the cell colony GFP(+), and analyzes the results obtained, to form the measurement information concerned with the changes in membrane potential of the cell colony GFP(+) (step S9).

Figure 8:
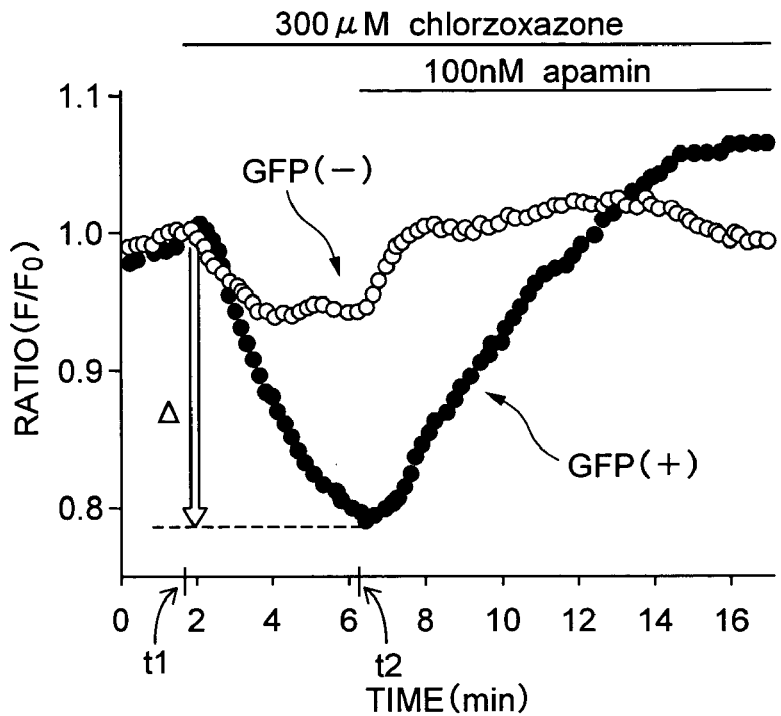
FIG. 8 is a graph showing changes with time in intensity of fluorescence emitted from cell colonies GFP(+) and GFP(−).

In FIG. 8, plotted as abscissa is the time (min) having lapsed after the image capture of the fluorescent image B (FIG. 7) is started (hereinafter "start of measurement"). As ordinate, plotted is the ratio of the fluorescence intensity Fo of the fluorescence emitted from the cell colony GFP(+) at the time of the start of measurement to the fluorescence intensity F of the fluorescence emitted from the cell colony GFP(+) at any arbitrary time having lapsed, F/Fo.

For comparison, changes with time (artifact) in the intensity of fluorescence emitted from the cell colony GFP(−) containing no expressed cell at all are also shown together in FIG. 8. Two horizontal lines further shown in FIG. 8 at its upper part represent the time for which the chemical substances (chlorzoxazone, apamin) are kept included in the culture solution of the specimen. The left ends of the horizontal lines corresponds to the timing t1 and t2 at which the chemical substances are introduced.

The following can be seen from the changes with time (FIG. 8) in the intensity of fluorescence emitted from the cell colony GFP(+). That is, upon introduction of the 300 μM chlorzoxazone (rSK2 channel opener), a remarkable decrease in fluorescence intensity (i.e., overpolarization) appears in the cell colony GFP(+), compared with the cell colony GFP(−). Further, upon introduction of the 100 nM apamin (rSK2 channel inhibitor), the above decrease in fluorescence intensity is restrained.

The measurement information concerned with the changes in membrane potential of the cell colony GFP(+) is formed, e.g., in the following way: Of the changes with time (FIG. 8) of fluorescence intensity of the cell colony GFP(+), the fluorescence intensity before introduction of the 300 μM chlorzoxazone is assumed as 100%, where the fluorescence intensity (%) after lapse of certain time after introduction of the 300 μM chlorzoxazone (the timing at which the second chemical substance 100 nM apamin is introduced) is found, and its response rate Δ(%) (per cent decrease) is found. Thus, the intended information is formed.

In the example shown in FIG. 8, it follows that a measurement result that the introduction of 300 μM chlorzoxazone into the specimen where the rSK2 channel has been made expressed brings about a decrease in fluorescence intensity by about 20% has been obtained as the measurement information concerned with the changes in membrane potential.

Figure 9:
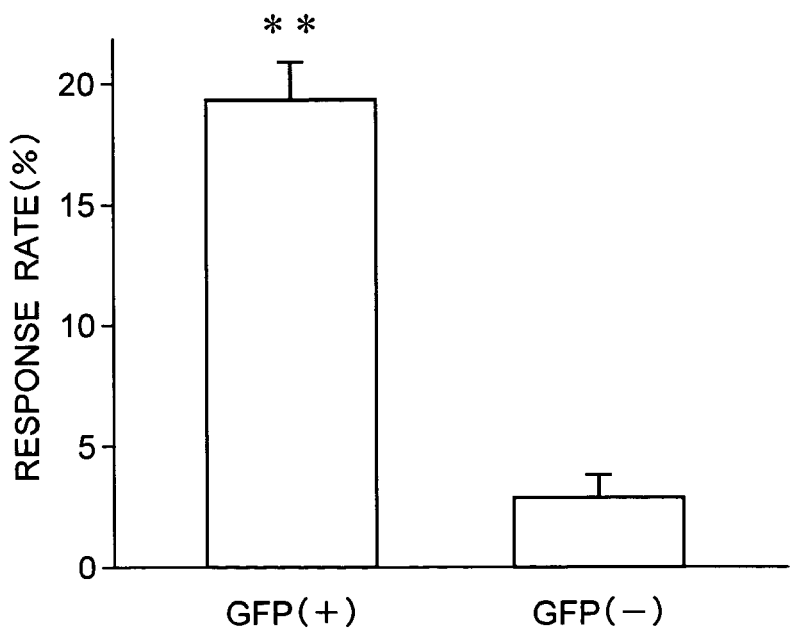
FIG. 9 shows the results of measurement made using specimens prepared in five different laboratory dishes.

The same measurement as the above but using each of specimens prepared in five different laboratory dishes 21 has further been made to obtain the results (FIG. 9) as explained below. In FIG. 9, as ordinate, plotted is the response rate (%) of fluorescence intensity upon introduction of the 300 μM chlorzoxazone, assuming as 100% the fluorescence intensity before introduction of the 300 μM chlorzoxazone. In comparison of measurement results of each of the two cell colonies GFP(+) and GFP(−), it has been allowed as a result of Student's t-examination that there is a significant difference of **$p<0.01$.

As is clear from this specific example as well, even when the cell colony GFP(−) containing no expressed cell at all is present in the measurement visual field, any false fluorescence intensity coming from the cell colony GFP(−) is not detected, and only substantial fluorescence intensity coming from the cell colony GFP(+) containing at least one expressed cell is selectively detected. Hence, the measurement information of membrane potential changes caused by chemical substances (e.g., the response rate (%) of fluorescence intensity) can be determined in a high sensitivity and a good reproducibility.

In addition, even when the expressed cells in the specimen are in a low proportion (low expression efficiency), or even when the expression of the target protein (e.g., rSK2 channel) is transient, the membrane potential changes caused by chemical substances can be measured in a high sensitivity and a good reproducibility. Hence, the operation to prepare specimens can surely be simplified.

In the above First Embodiment, the noted colony (the cell colony 23(1) shown in FIGS. 3A and 3B) is specified by the processing of steps S5 to S7 shown in FIG. 4. The present invention is by no means limited to this example.

For example, instead of extracting all the high-brightness regions (cell colony regions b) from one fluorescent image B in the step S6, only a cell colony region b that contains at least one expressed-cell region a extracted in the step S5 may directly be extracted from the fluorescent image B. In this case, the processing in the step S7 is omitted.

In the above First Embodiment, the processing (steps S5 to S9) to form the measurement information of membrane potential changes caused by chemical substances is performed after the fluorescent images A and B have all been captured through the steps S1 to S4 shown in FIG. 4. The present invention is by no means limited to this example.

For example, the extraction of the expressed-cell region a from the fluorescent image A (the processing in the step S5) may be performed immediately after the fluorescent image A has been captured in the step S2. In this case, the control unit 20 can execute the processing of steps S3, S4, S6 and so on, after making sure that expressed cell 22a is present in the measurement visual field 10a. Hence, the changes in membrane potential can be measured in a good efficiency. However, making sure of the presence of the expressed cell 22a may also be performed on the display unit.

Second Embodiment

As Second Embodiment of the present invention, an example of an intracellular-reaction measuring apparatus with which the membrane potential changes caused by chemical substances can be measured in a high sensitivity and a good reproducibility is described below.

The intracellular-reaction measuring apparatus of Second Embodiment is a apparatus in which the image processing unit 18 performs the processing of steps (S11) to (S13) described later, between the steps S7 and S8 of the procedure (FIG. 4) of measuring the membrane potential changes in the intracellular-reaction measuring apparatus 10 described above. Incidentally, in Second Embodiment, the image processing unit 18 also corresponds to "calculation means" and "sorting means" referred to in claims.

In this connection, in the intracellular-reaction measuring apparatus 10 described above, the image processing unit 18 selects, in the fluorescent image B, the cell colony region b containing at least one expressed-cell region a(step S7), whereupon it performs the processing of the step S8 and following steps, noting the cell colony region b thus selected.

In the intracellular-reaction measuring apparatus of Second Embodiment, the image processing unit 18 selects the cell colony region b containing at least one expressed-cell region a, as a result of the processing of the step S7, whereupon it executes the following processing of steps (S11) to (S13) before it proceeds to the step S8.

Step (S11):

First, the image processing unit 18 calculates the proportion of the expressed-cell region a for each cell colony region b (containing at least one expressed-cell region a) selected in the step S7. This corresponds to the processing to calculate the proportion of the expressed-cell region a for each noted colony (containing at least one expressed cell 22a) present in the measurement visual field 10a.

Step (S12):

Next, it calculates the number of all cell regions for each cell colony region b (containing at least one expressed-cell region a) selected in the step S7. This corresponds to the processing to calculate the number of all cells for each noted colony (containing at least one expressed cell 22a) present in the measurement visual field 10a.

Step (S13):

Finally, it sorts out, of the noted colonies (each containing at least one expressed cell 22a) present in the measurement visual field 10a, a noted colony containing expressed cells 22a in a proportion higher than 20% and also having the number of cells of less than 20 in total.

Thereafter, it executes the processing of the steps S8 and following steps shown in FIG. 4, to selectively detects the intensity of fluorescence emitted from the noted colony sorted out through the above processing of steps (S11) to (S13) (the cell colony containing cells in a relatively small number in total and expressed cells in a high proportion), and thereby determines the measurement information of membrane potential changes caused by chemical substances (e.g., the response rate Δ of fluorescence intensity). Hence, this brings more improvement in measurement sensitivity and reproducibility.

Figure 10:
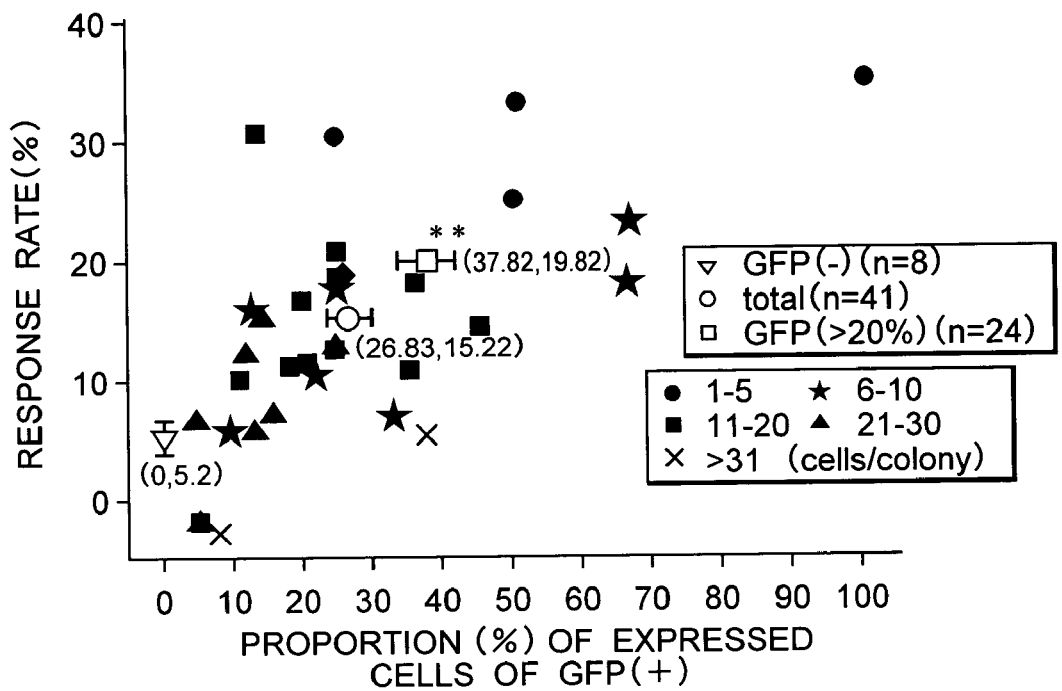
FIG. 10 is a graph showing the relationship between the proportion (%) of expressed cells of a cell colony GFP(+) and the response rate (%) of fluorescence intensity upon introduction of chemical substances.

Here, in each of various cell colonies GFP(+), the relationship between the proportion (%) of expressed cells (abscissa) and the response rate (%) (per cent decrease) of fluorescence intensity upon introduction of 300 μM chlorzoxazone (ordinate) has been examined to obtain the results shown in FIG. 10. The number of cell colonies GFP(+) on which this relationship has been examined is 41.

In FIG. 10, measurement points are grouped by marks made different for each number n of total cells of cell colonies GFP(+) [black circle (●): n=1 to 5; black star (★): n=6 to 10; black square (■): n=11 to 20; black triangle (▲): n=21 to 30; cross (X): n>31]. As can be seen from these measurement points, the response rate (%) of fluorescence intensity in respect to chemical substances is small in cell colonies (cross, black triangle) having a large number n of total cells. Accordingly, in Second Embodiment, noted are cell colonies (black circle, black star, black square) having a number n of total cells which is smaller than 20.

A measurement point marked by a white circle (○) in FIG. 10 further represents an average value and a standard error in all (41) cell colonies GFP(+). The average value of the proportion of expressed cells has been found to be 26.8%; and the average value of the response rate of fluorescence intensity upon introduction of chemical substances, 15.2%.

A measurement point marked by a white square (□) in FIG. 10 represents an average value and a standard error in twenty-four (24) cell colonies GFP(+) containing expressed cells in a proportion of 20% or more. The average value of the proportion of expressed cells has been found to be 37.82%; and the average value of the response rate of fluorescence intensity upon introduction of chemical substances, 19.8%.

A measurement point marked by an inverted white triangle (∇) in FIG. 10 is a point shown for comparison with the above measurement points marked by the white circle (○) and white square (□), and is concerned with cell colonies GFP(−) containing no expressed cells at all. That is, it represents an average value and a standard error in eight (8) cell colonies GFP(−) obtained from different laboratory dishes 21. In the case of the cell colonies GFP(−), the average value of the response rate (artifact) of fluorescence intensity upon introduction of chemical substances has been found to be 5.2%.

From these measurement points marked by the white circle (○), white square (□) and inverted white triangle (∇), the following can be seen. That is, the cell colonies GFP(+) containing expressed cells in a proportion of 20% or more may be sorted out to find the response rate of fluorescence intensity upon introduction of chemical substances, whereby the reaction of four times that of the artifact [response rate of fluorescence intensity in the cell colonies GFP(−)] can be detected. Incidentally, the measurement point marked by white circle (○) has a significant difference at a risk factor of 0.1%.

In the above Second Embodiment, both the proportion of expressed cells and the number of total cells are compared with each standard value in the processing of the step (S13) to sort out the noted colony [cell colony GFP(+)]. The present invention is by no means limited thereto. Only the proportion of expressed cells may be compared with the standard proportion to sort out the noted colony, or only the number of total cells may be compared with the standard number to sort out the noted colony.

In addition, in the above Second Embodiment, the artifact in introducing chemical substances can be measured on the basis of the response rate of fluorescence intensity of the cell colonies GFP(−) containing no expressed cells at all (e.g., FIG. 8, FIG. 9, the measurement point marked by inverted white triangle (∇) in FIG. 10). Hence, the response rate of fluorescence intensity upon introduction of chemical substances in the cell colony GFP(+) containing expressed cells can very accurately be measured by comparing it with this artifact.

Herein, the artifact does not act directly on the target rSK2 protein, and involves all reactions that change the fluorescence intensity of DiBAC$_4$(5). Hence, it involves reactions like side effect that changes the membrane potential indirectly, not by direct action of chemical substances on the target rSK2 protein but by other action (e.g., by inhibiting the production of cell energy). Thus, changes in fluorescence intensity which are caused by chemical substances in the cell colony GFP(-) also provides important information when the intracellular reactions are detected.

Third Embodiment

As Third Embodiment of the present invention, an example of an intracellular-reaction measuring apparatus with which the membrane potential changes caused by chemical substances can be measured in a high sensitivity and a good reproducibility is described below.

The intracellular-reaction measuring apparatus of Third Embodiment is, different from the above First Embodiment and Second Embodiment, an apparatus with which the membrane potential changes caused by chemical substances are measured using a specimen in which a plurality of cells stand adherent to one another to have substantially the shape of a sheet or sheets. Hence, this apparatus is so constructed that, in place of the steps S6 and S7 of the procedure (FIG. 4) of measuring the membrane potential changes in the intracellular-reaction measuring apparatus 10 described above, the image processing unit 18 performs the processing of steps (S21) to (S23) described later. Contingent to this, there is also some alteration (described later) in the step S8 shown in FIG. 4, carried out after the processing of steps (S21) to (S23).

Here, before the processing of steps (S21) to (S23) is specifically described, how to prepare the specimen is described on ahead. The specimen is prepared by the above procedure of steps (1) to (3) of which the step (2) has been replaced with the following step (4).

Step (4):

When the culture cells into which the expression vector has been incorporated and thereby the gene of target protein (e.g., rSK2 channel) and the gene of fluorescent protein (e.g., GFP) have been incorporated are cultured in the laboratory dish 21, the culture conditions and culture time are changed to culture the cells in such a way that cell colonies adhere to one another.

As the result, it follows that in the specimen held in the laboratory dish 21 a plurality of culture cells (e.g., HEK23 cells) are contained in the state they adhere to one another (what is called a confluent state). In some culture cells, the target protein and the fluorescent protein stand expressed simultaneously. This expression is in an expression efficiency of, e.g., approximately from 20% to 30%.

The measurement of changes in membrane potential that is made using the specimen having been prepared through the procedure following the steps (1), (4) and (3) in this order is made according to the procedure that, after the steps S1 to S5, the image processing unit 18 executes the processing of steps (S21) to (S23) described later, and finally executes the same processing of the steps S8 and S9.

In the following description, reference is made to a phase-contrast photomicrograph (FIG. 11) of the specimen. As can be seen from this photograph, a plurality of culture cells stand confluent in the measurement visual field. One side of the photomicrograph is about 180 μm in length.

A fluorescent image A (FIG. 12) is an image on the basis of fluorescence emitted from the GFP present in the measurement visual field, and is an image of expressed cells (HEK293 cells in which the rSK2 channel and the GFP have been expressed simultaneously). When the control unit 20 captures the fluorescent image A (FIG. 12), the excitation light is set to have a center wavelength of 480 nm. In the filter set, a filter capable of transmitting light with wavelengths ranging from 510 nm to 540 nm is used as the fluorescent filter 15.

Further, when the control unit 20 captures fluorescent images B (FIG. 13) repeatedly in the same visual field through the steps S3 and S4, the excitation light is set to have a center wavelength of 560 nm. In the filter set, a filter capable of reflecting light with wavelengths shorter than 590 nm and transmitting light with wavelengths of 590 nm and longer is used as the dichroic mirror 13. The fluorescent images B (FIG. 13) are images on the basis of fluorescence emitted from the membrane-potential-sensitive fluorescent dye [DiBAC$_4$(5)], and are images of the plurality of culture cells standing confluent.

Figure 11:
FIG. 11 is a phase-contrast photomicrograph of a specimen.
Figure 12:
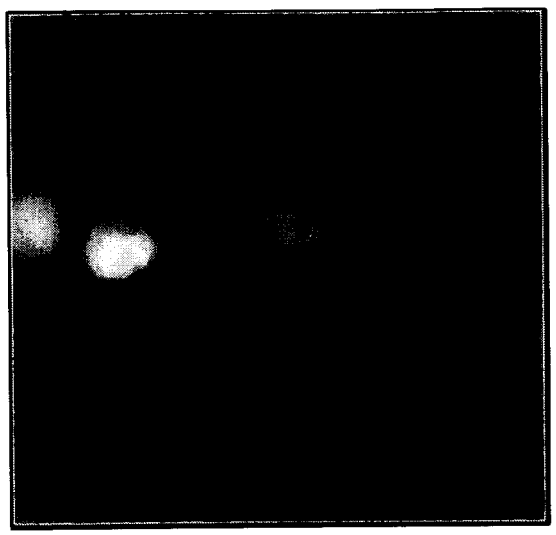
FIG. 12 is a photograph of a fluorescent image captured on the basis of fluorescence emitted from GFP.
Figure 13:
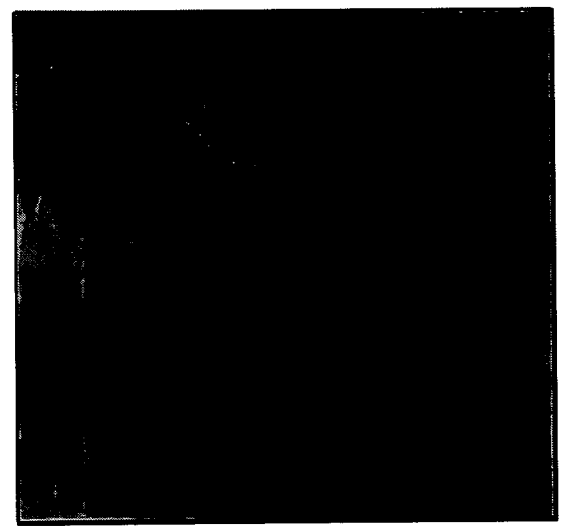
FIG. 13 is a photograph of a fluorescent image captured on the basis of fluorescence emitted from $DiBAC_4(5)$.

As can be seen from the photographs shown in FIGS. 11 to 13, the expressed cells of the specimen stand gathered at the upper left part. Now, the image processing unit 18 extracts from the fluorescent image A (FIG. 12) all high-brightness regions (expressed-cell regions a) corresponding to the expressed cells, for each expressed cell. Then, it proceeds to the next processing of the step (S21). In the case shown in FIG. 12, six expressed-cell regions a are present in the fluorescent image A.

Step (S21):

First, the image processing unit 18 selects an arbitrary one-image (an image before introduction of chemical substances) from among a large number of fluorescent images B (FIG. 13). Then, it detects the brightness information of the fluorescent image B selected, to thereby extract all high-brightness regions corresponding to expressed cells (hereinafter "culture cell region(s)") in the measurement visual field.

Step (S22):

Next, using the results of extraction in the steps S5 and S6, the image processing unit 18 superimposes the fluorescent image A having the expressed-cell region(s) a and the fluorescent image B having the culture cell regions. Then, in the culture cell region, it sets some arbitrary regions containing at least one expressed cell region a (e.g., see two elliptic regions in FIG. 14). These regions are candidate regions for finding the response rate of fluorescence intensity upon introduction of chemical substances.

Figure 14:
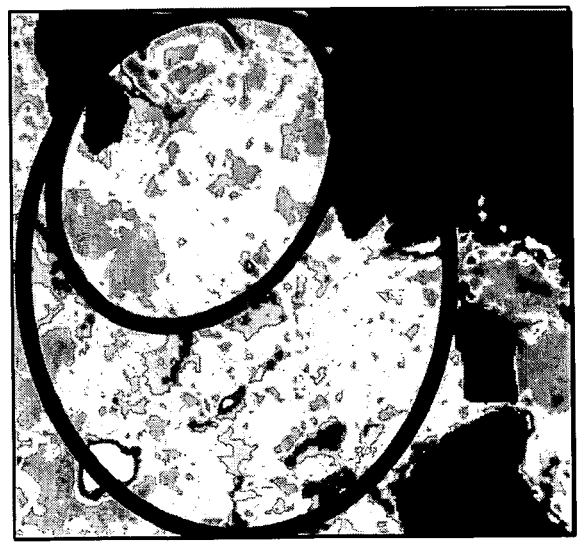
FIG. 14 is a photograph of an artificially color-displayed image, in which a fluorescent image captured on the basis of fluorescence emitted from $DiBAC_4(5)$ is represented as its ratio to a fluorescent image at the time the measurement is started.

FIG. 14 is an artificial color display of the result obtained when the brightness value (α fluorescence intensity) of each pixel of the fluorescent image B captured immediately before introduction of chemical substances is divided by the brightness value of each pixel of the fluorescent image B captured at the time of the start of measurement. The division of brightness value is made on mutually the same pixel in the same visual field.

Step (S23):

Next, the image processing unit 18 calculates the proportion of the expressed cell region(s), for each plurality of candidate regions (e.g., the two elliptic regions in FIG. 14) (containing at least one expressed cell region a) set in the step S22. Then, finally, it sorts out, of the plurality of candidate regions, a region where the proportion of the expressed cell region(s) is higher than 20%.

For example, in the case shown in FIG. 14, the smaller (red) elliptic region is sorted out. In this region, about 20 culture cells in total are contained. Also, in the same region, the number of the expressed cell regions a (see FIG. 12) is about 6. Hence, the expressed cell regions a are in a proportion of about 30%.

Thereafter, the image processing unit 18 executes the same processing as that of the steps S8 and S9 to selectively detect fluorescence intensity on the basis of the brightness information of the noted region (the region where the expressed cells are in a higher proportion) (hereinafter "high-expressed region") and at the same time finds changes with time in fluorescence intensity (FIG. 15), and analyzes the results obtained, to form the measurement information of the membrane potential changes caused by chemical substances (e.g., response rate of fluorescence intensity).

Figure 15:
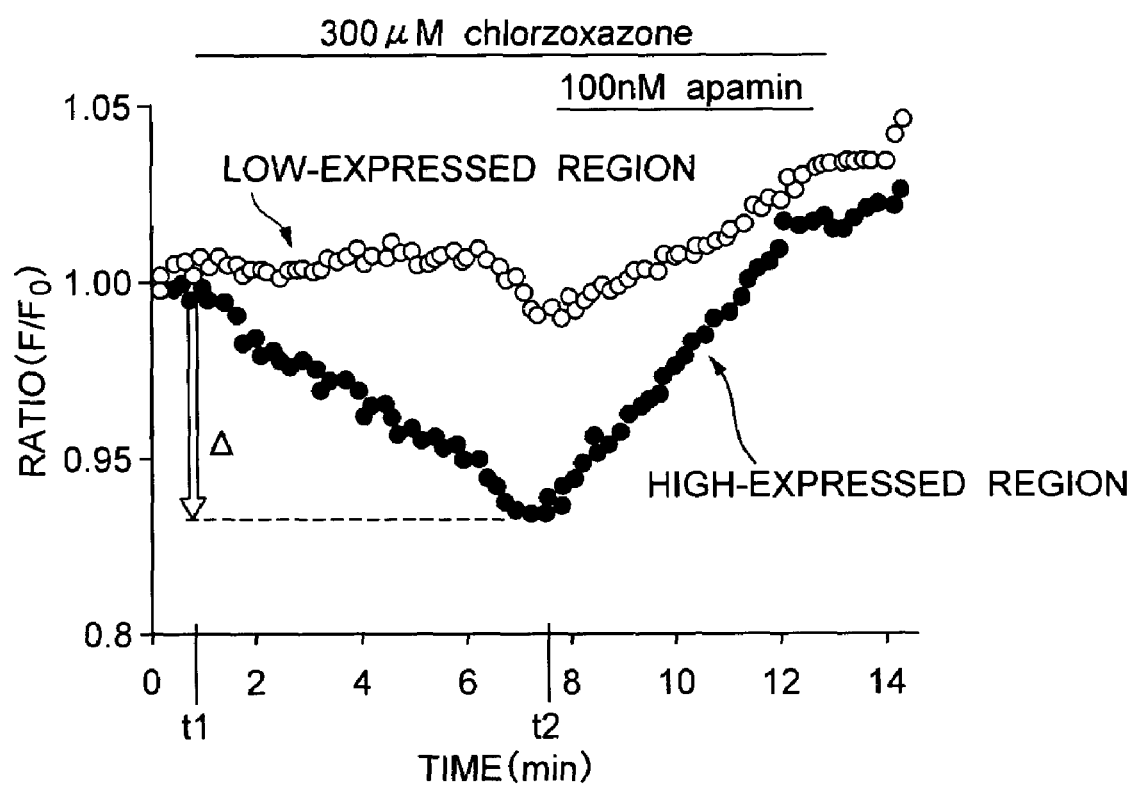
FIG. 15 is a graph showing changes with time in intensity of fluorescence emitted from a high-expression region and that from a low-expression region.

In FIG. 15, plotted as abscissa is the time (min) having lapsed after the start of measurement. As ordinate, plotted is the ratio of the fluorescence intensity Fo of the fluorescence emitted from the high-expressed region at the time of the start of measurement to the fluorescence intensity F of the fluorescence emitted from the high-expressed region at any arbitrary time having lapsed, F/Fo.

Two horizontal lines further shown in FIG. 15 at its upper part represent the time for which the chemical substances (chlorzoxazone, apamin) are kept included in the culture solution of the specimen. The left ends of the horizontal lines correspond to the timing t1 and t2 at which the chemical substances are introduced. In this Third Embodiment, the timing t2 is set to be 8 minutes after the start of measurement.

For comparison, also shown in FIG. 15 are changes with time in the intensity of fluorescence emitted from a region not sorted out in the step (S23) (e.g., the larger (black) elliptic region in FIG. 14) (hereinafter "low-expressed region"). The low-expressed region is a broad region corresponding to substantially the whole measurement visual field, in which the expressed cell regions a (see FIG. 12) are in a proportion of less than 10%.

The changes with time in fluorescence intensity that are attributable to this low-expressed region are measured equally to a conventional case in which an average-level fluorescence intensity in the measurement visual field is measured. As can be seen from FIG. 15, any fall in intensity or rise in intensity caused by introduction of chemical substances is little seen in the changes with time in fluorescence intensity in the low-expressed region. That is, it is very difficult to accurately determine the measurement information of membrane potential changes caused by chemical substances if the changes with time in fluorescence intensity is examined by conventional methods.

On the other hand, in the changes with time in fluorescence intensity in the high-expressed region, how the fluorescence intensity falls upon introduction of 300 μM chlorzoxazone and how the fluorescence intensity rises upon introduction of 100 nM apamin are clearly seen. Such changes in the high-expressed region indicate that the chemical substances have caused changes in membrane potential and as the result thereof the fluorescence intensity of the membrane-potential-sensitive fluorescent dye $DiBAC_4(5)$ has changed.

Hence, the measurement information of membrane potential changes caused by chemical substances (e.g., response rate Δ of fluorescence intensity) can be determined in a high sensitivity and a good reproducibility by sorting out the high-expressed region (e.g., expression efficiency: 30%) in the step (S23) and selectively detecting only the substantial fluorescence intensity coming from this high-expressed regions.

In the above Third Embodiment, the fluorescence intensity coming from the high-expressed region set in the measurement visual field 10a is detected. The present invention is by no means limited to this. For example, the proportion of expressed cells in the whole measurement visual field may be calculated, and, where this proportion is larger than the standard proportion, the intensity of fluorescence emitted from the whole measurement visual field may be detected without setting the high-expressed region described above.

In the above Third Embodiment, the changes in membrane potential are also measured using the specimen in which a plurality of culture cells stand adherent. However, also in the case when a plurality of cell colonies are contained in the specimen in a non-contact state (see FIG. 2), the procedure of measurement in Third Embodiment may be applied as long as individual cell colonies are relatively large and culture cells stand adherent to one another in the measurement visual field.

In addition, in the above First to Third Embodiments, the fluorescence intensity coming from the cell colony containing at least one expressed cell or the fluorescence intensity coming from the high-expressed region described above is selectively detected. The present invention is by no means limited to this. For example, likewise correct results can be obtained also when, e.g., the intensity of fluorescence emitted from the expressed cell(s) per se present in the measurement visual field is selectively detected.

However, with a decrease in the number of cells on which the fluorescence intensity is to be detected, the total fluorescence intensity may decrease correspondingly and also results with large scattering may come which come from the condition of each cell. Accordingly, the fluorescence intensity coming from the cell colony or high-expressed region is selectively detected as in the above First to Third Embodiments. This can secure a larger number of cells to be detected, and enables measurement in a higher accuracy.

Fourth Embodiment

As Fourth Embodiment of the present invention, an example of an intracellular-reaction measuring apparatus with which the ion concentration changes caused by chemical substances can be measured in a high sensitivity and a good reproducibility is described below. In this connection, "ions" referred to in changes in ion concentration refer to ions present within a cell, as exemplified by calcium ions, hydrogen ions, magnesium ions, sodium ions, potassium ions and chloride ions.

The specimen on which the measurement is to be made is prepared by the above procedure of steps (1) to (3) of which the step (3) has been replaced with the following step (5). It does not matter whether the plurality of culture cells (e.g., HEK293 cells) in the laboratory dish 21 have formed cell colonies in a mutually non-contact state or stand confluent after the culturing in the procedure of step (2).

Step (5):

At the final stage of the operation to prepare the specimen, a fluorescent probe for measuring intracellular reactions is introduced all over into the specimen (containing a plurality of cell colonies) held in the laboratory dish 21. The fluorescent probe used here is an ion-concentration-sensitive fluorescent dye. This fluorescent dye may include those for measuring the absolute value of ion concentration and those for measuring relative changes in ion concentration.

For example, where changes in calcium ion concentration are measured, Fura-2/AM (Molecular Probes, USA) is used as the fluorescent probe. To introduce the Fura-2 into the specimen, in an incubator the culture cells (HEK293 cells may be immersed for about 30 minutes in a physiological saline solution containing this Fura-2 in a concentration of 100 nM. The culture cells taken out of the incubator are washed with a physiological saline solution. During the measurement of changes in ion concentration, the laboratory dish 21 is filled with the physiological saline solution.

In order to measure the changes in ion concentration using the specimen thus prepared, in the intracellular-reaction measuring apparatus 10 of Fourth Embodiment, a filter set best suited for detecting the fluorescence emitted from GFP and a filter set best suited for the detection of fluorescence emitted from Fura-2 are set switchable. The filter set for the GFP is the same as that described already.

The filter set for the Fura-2 is a combination of a first excitation filter 12 capable of transmitting light with wavelengths of around 340 nm, a second excitation filter 12 capable of transmitting light with wavelengths of around 380 nm, a dichroic mirror 13 capable of reflecting light with wavelengths shorter than 400 nm and transmitting light with wavelengths of 400 nm and longer, and a fluorescence filter 15 capable of transmitting light with wavelengths of around 510 nm. As to the first and second excitation filters 12, either of them is inserted.

Then, in the intracellular-reaction measuring apparatus of Fourth Embodiment, in the first place, like the above steps S1 and S2 shown in FIG. 4, the control unit 20 captures the fluorescent image A of expressed cells (HEK293 cells in which the rSK2 channel and the GFP stand expressed simultaneously) on the basis of the fluorescence emitted from the GFP present in the measurement visual field.

Next, it changes the filter set from that for GFP to that for Fura-2 and at the same time sets the excitation filter 12 to "340 nm" to capture a fluorescent image C(1) on the basis of the fluorescence emitted from the Fura-2 present in the measurement visual field. It further changes the excitation filter 12 to "380 nm" to capture a like fluorescent image C(2). With these two fluorescent images C(1) and C(2) as one set, it repeats the image capture of fluorescent images C(1) and C(2) at intervals of 10 seconds.

Capturing the fluorescent images C(1) and C(2) repeatedly, the control unit 20 also introduces two kinds of chemical substances (chlorzoxazone, apamin) into the specimen halfway and at the preset timing. Further, using one set of fluorescent images C(1) and C(2), it divides the brightness value of each pixel of the fluorescent images C(1) by the brightness value of each pixel of the fluorescent images C(2) to form distribution images D of calcium ion concentration.

Thereafter, upon completion of the image capture of fluorescent image A and fluorescent images C(1) and C(2) and formation of the distribution images D of calcium ion concentration, the image processing unit 18 performs the same processing as that in the step S4 shown in FIG. 4, to extract all high-brightness regions (expressed cell regions a) corresponding to expressed cells.

Next, the image processing unit 18 superimposes the fluorescent image A having the expressed-cell regions a and the distribution images D of calcium ion concentration which has been formed from the fluorescent images C(1) and C(2), to selectively detect partial information corresponding to the expressed cell regions a, from the brightness information of the distribution images D, and calculate its average brightness (i.e., fluorescence intensity) for each distribution image D.

Finally, it analyzes changes with time in the fluorescence intensity having been calculated for each distribution image D, to form measurement information concerned with changes in ion concentration of expressed cells. Where the fluorescence intensity has increased before and after the introduction of chemical substances, the calcium ion concentration in the expressed cells has increased, and hence it is deemed that the chemical substances have an effect.

Thus, in the intracellular-reaction measuring apparatus of Fourth Embodiment, the intensity of fluorescence emitted from expressed cells present in the measurement visual field is selectively detected to form the measurement information of ion concentration changes caused by chemical substances (e.g., find the per cent increase in fluorescence intensity). Hence, the changes in ion concentration can be measured in a high sensitivity and a good reproducibility.

Fifth Embodiment

As Fifth Embodiment of the present invention, an example is described in which the intracellular-reaction measuring apparatus 10 of First Embodiment is applied to screening carried out in the course of developing pharmaceuticals. In this case, a 96-hole microplate is used as a culture container for a specimen, and is placed on the stage of the fluorescent microscope (11-16). The microplate also has a transparent bottom.

In preparing the specimen, a solution containing culture cells (e.g., HEK293 cells) in a concentration of $10^5$ cells/ml is poured in each well of the microplate in an appropriate quantity (e.g., 150 µl each), except that only a culture solution is put in one well, namely, this well contains no culture cell.

Into the solution in each well, a gene of the rSK2 channel and a gene of the GFP are introduced by calcium phosphate coprecipitation, and are cultured at 37° C. for 36 to 48 hours. At the final stage of preparation, the membrane-potential-sensitive fluorescent dye [DiBAC$_4$(5)] is also over all introduced into the specimen in each well.

The procedure of measurement using the microplate is basically the same as that shown in FIG. 4.

In respect of the well containing no culture cell, too, the control unit 20 captures a fluorescent image A0 using the filter set for GFP, and then captures a fluorescent image B0 using the filter set for DiBAC$_4$(5). These fluorescent images A0 and B0 are used for correction, as background light images. That is, these are used to subtract and remove the background light from the brightness information of fluorescent images in the subsequent respective wells. Here, the background light refers to fluorescence coming from things other than the specimen, such as the culture solution and the microplate.

Similarly, in respect of other wells (those containing culture cells), the control unit 20 captures the fluorescent image A using the filter set for GFP, and then captures the fluorescent images B using the filter set for DiBAC$_4$(5), at intervals of a constant time (e.g., 10 seconds). During the image capture of fluorescent images B, it also adds to each cell 50 µl each of chemical substances different in kinds and concentration.

After the image capture of all the fluorescent images A and B has been completed in this way, the brightness information of these fluorescent images A and B is corrected by the brightness information of the background light images (fluorescent images A0 and B0). Then, using fluorescent images A and B having been corrected, the measurement information of membrane potential changes caused by chemical substances (response rate of fluorescence intensity) is formed for each well.

As described already, the substantial fluorescence intensity coming from the noted colonies containing expressed cells is selectively detected, and hence the measurement information of membrane potential changes caused by chemical substances (e.g., response rate Δ) in each well can be obtained in a high sensitivity and a good reproducibility. Thus, any differences in reactions of each chemical substance can clearly be analyzed, making it possible to effect screening in a good efficiency. Incidentally, the chemical substance introduced into a well in which the response rate of fluorescence intensity has been recognized to be significant is deemed to have a high effect on the rSK2 channel.

Incidentally, in screening the action of chemical substance by the use of the microplate, it inevitably takes a fairly long time until the measurement of changes in ion concentration is completed on all the wells, if the control unit 20 captures the fluorescent images B at intervals of a constant time while introducing the chemical substances.

Accordingly, it is preferable to lessen the number of times of capturing the fluorescent images B and perform image capture "at least twice". For example, when the image capture is performed twice, the first-time image capture is performed before the chemical substances are introduced and the second-time image capture is performed at a certain time after the chemical substances have been introduced. Incidentally, the timing of introducing chemical substances is detectable in the control unit 20.

Thus, when the control unit 20 captures for each cell the fluorescent images B at intervals of a constant time before and after the introduction of chemical substances, it can perform image capture of other well, so that the measurement time can be shortened as a whole.

For example, when eleven wells are measurement targets, the control unit 20 first captures fluorescent images A and B in each well one by one in order, and then introduces chemical substances in each well in order. The time taken to introduce chemical substances into all eleven wells is about 3 minutes. The time taken to introduce chemical substances into each well is kept recorded. Then, after about 5 minutes, the control unit 20 performs second-time image capture of fluorescent images B in order.

As the result, it can capture two fluorescent images B for each well in a good efficiency, and can shorten the whole measurement time. Hence, a high-speed and high-efficiency system for examining actions of chemical substances can be set up.

In the above Fifth Embodiment, the intracellular-reaction measuring apparatus 10 of First Embodiment is applied to screening. The present invention is by no means limited to this. Besides such an apparatus, the intracellular-reaction measuring apparatus of Second to Fourth Embodiments may also be applied to the screening.

Modifications

In the above First to Fourth Embodiments, examples have been described in which the fluorescent images B [or the fluorescent images C(1) and C(1)] are captured at intervals of a constant time. The present invention is also applicable to a case in which, like Fifth Embodiment, the fluorescent images [or the fluorescent images C(1) and C(2)] are captured before and after introduction of chemical substances each time (at a preset timing).

In all the embodiments described above, the control unit 20 controls the laboratory dish 21. The present invention is by no means limited to this. For example, the present invention is applicable also when a laboratory dish for manual operation is used. In such a case, it is preferable to provide a switch for detecting the timing at which chemical substances are introduced through the laboratory dish.

In addition, in all the embodiments described above, the intracellular reactions (changes in membrane potential and changes in ion concentration) are measured on the basis of the intensity of fluorescence emitted from specimens. The present invention is by no means limited to this. Besides such fluorescence, the present invention is applicable also to a case in which the intracellular reactions are measured on the basis of the intensity of chemical luminescence or biological luminescence emitted from specimens. In this case, the luminescence is self-luminescence, and hence it is unnecessary to irradiate specimens with excitation light.

In all the embodiments described above, examples have also been described in which the intracellular reactions (changes in membrane potential and changes in ion concentration) caused by chemical substances are measured. Any intracellular reactions caused by factors other than chemical substances (e.g., environmental changes such as temperature changes) may also be measured.

In addition, in all the embodiments described above, the fluorescent protein GFP is used in order to verify the presence of target protein. The presence of protein may also be verified using an antibody to that protein, having been labeled with a fluorescent dye.

As having been described above, the present invention enables improvement in the sensitivity and reproducibility in the measurement of intracellular reactions, without making any complicated operation for preparing specimens.

What is claimed is:

1. An intracellular-reaction measuring apparatus for measuring intracellular reactions after introduction of chemical substances by the use of a specimen in which a plurality of cells which stand adherent to one another, are contained, the apparatus comprising:

photo-detecting means which detects the intensity of first light emitted from said cells in accordance with the presence of a stated protein and the intensity of second light emitted from said cells notwithstanding that a stated protein is present or not therein;

a controller that selectively sets into a measuring optical path a first filter member for making the photo-detecting means detect said first light and a second filter member for making the photo-detecting means detect said second light;

a first extracting member that extracts expressed cells emitting said first light as an image on the basis of a detection signal of said first light detected by said photo-detecting means when the controller sets the first filter into the measuring optical path;

a second extracting member that extracts all cells emitting said second light as an image on the basis of a detection signal of said second light detected by said photo-detecting means when the controller sets the second filter into the measuring optical path;

a specifying member that superposes the image of the expressed cells extracted by the first extracting means and the image of all cells extracted by the second extracting means and specifies a cell region in which said expressed cells extracted by the first extracting member are contained with a higher proportion than a stated standard, among cell regions containing said all cells inclusive of cells having no stated protein extracted by the second extracting member; and an analyzing member which analyzes said intracellular reactions on the basis of the detected signal, which is detected by said photo-detecting means, of said second light emitted from said cells in which said stated protein is present and the second light emitted, in accordance with intracellular reactions induced by the stated protein, from said cells in which said stated protein is not present.

2. The intracellular-reaction measuring apparatus according to claim 1, further comprising:

a chemical-substance introduction means for introducing into said cells chemical substances which target said protein.

3. The intracellular-reaction measuring apparatus according to claim 1, wherein the second extracting member extracts said all cells on the basis of the detected signal of said second light detected by said photo-detecting means.

4. The intracellular-reaction measuring apparatus according to claim 1, wherein the second extracting member extracts said all cells from a picture image of said sample captured by a phase-contrast microscope.

5. The intracellular-reaction measuring apparatus according to claim 1, wherein said photo-detecting means is a cooled imaging device, said cooled imaging device captures a fluorescent image by detecting fluorescence from said cells, and said first and second extracting members extract cells on the basis of brightness information of said fluorescent image.

6. An intracellular-reaction measuring apparatus for measuring intracellular reactions after introduction of chemical substances by the use of a specimen in which a plurality of cells are contained, as a plurality of cell colonies in a non-contact state, the apparatus comprising:

photo-detecting means which detects the intensity of first light emitted from said cells in accordance with the presence of a stated protein and the intensity of second light emitted from said cells notwithstanding that a stated protein is present or not therein;

a controller that selectively sets into a measuring optical path a first filter member for making the photo-detecting means detect said first light and a second filter member for making the photo-detecting means detect said second light;

a first extracting member that extracts expressed cells emitting said first light as an image on the basis of a detection signal of said first light detected by said photo-detecting means when the controller sets the first filter into the measuring optical path;

a second extracting member that extracts all cell colonies emitting said second light as an image on the basis of a detection signal of said second light detected by said photo-detecting means when the controller sets the second filter into the measuring optical path;

a specifying member that superposes the image of the expressed cells extracted by the first extracting means and the image of all cells extracted by the second extracting means and specifies a cell colony in which said expressed cells extracted by the first extracting member are contained with a higher proportion than a stated standard, among said all cell colonies inclusive of cells not having the state protein extracted by the second extracting member, which includes cells not having the stated protein; and an analyzing member which analyzes said intracellular reactions after introduction of chemical substances on the basis of the detected signal, which is detected by said photo-detecting means, of said second light emitted, in accordance with intracellular reactions induced by the stated protein, from said cell colonies specified by the specifying member and the second light emitted from said cells in which said stated protein is not present, in accordance with intracellular reactions induced by the stated protein.

7. The intracellular-reaction measuring apparatus according to claim 6, further comprises a chemical-substance introduction device for introducing into said cells chemical substances which target said protein.

8. The intracellular-reaction measuring apparatus according to claim 6, wherein said second extracting member extracts said all cell colonies on the basis of the detection signal of the second light detected by said photo-detecting means.

9. The intracellular-reaction measuring apparatus according to claim 6, wherein the second extracting member extracts said all cell colonies from a picture image of said sample captured by a phase-contrast microscope.

10. The intracellular-reaction measuring apparatus according to claim 6, wherein said first extracting member counts the number of said expressed cells, said second extracting member counts the number of cells of each cell colony, and said specifying member specifies said cell colony which is extracted by the second extracting member and contains said expressed cells extracted by the first extracting member, and then said specifying member selects said cell colony containing said expressed cells extracted by the first extracting member with a larger number than said stated.standard with respect to the number of cells of said cell colony counted by the second extracting member.

11. The intracellular-reaction measuring apparatus according to claim 6, wherein said photo-detecting means is a cooled imaging device, said cooled imaging device captures a fluorescent image by detecting fluorescence from said cells, and said first and second extracting members extract cells on the basis of brightness information of said fluorescent image.

* * * * *